United States Patent
Pereira et al.

(10) Patent No.: US 10,653,450 B2
(45) Date of Patent: May 19, 2020

(54) SURGICAL TOOL CONTROL DEVICES AND METHODS OF USING THE SAME

(71) Applicant: Boston Scientific Scimed, Inc., Maple Grove, MN (US)

(72) Inventors: Peter J. Pereira, Mendon, MA (US); David Copeland, Minnetonka, MN (US); William J. Kane, Sutton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 102 days.

(21) Appl. No.: 15/276,011

(22) Filed: Sep. 26, 2016

(65) Prior Publication Data

US 2017/0086883 A1 Mar. 30, 2017

Related U.S. Application Data

(60) Provisional application No. 62/234,974, filed on Sep. 30, 2015.

(51) Int. Cl.
*A61B 17/42* (2006.01)
*A61B 90/50* (2016.01)
(Continued)

(52) U.S. Cl.
CPC ............... *A61B 17/42* (2013.01); *A61B 1/06* (2013.01); *A61B 50/20* (2016.02); *A61B 90/08* (2016.02); *A61B 90/50* (2016.02); *A61F 2/0009* (2013.01); *A61B 17/02* (2013.01); *A61B 2017/00212* (2013.01); *A61B 2017/00398* (2013.01); *A61B 2017/00477* (2013.01); *A61B 2017/00557* (2013.01); *A61B 2017/308* (2013.01); *A61B 2090/0817* (2016.02); *A61B 2090/309* (2016.02)

(58) Field of Classification Search
CPC . A61B 90/08; A61B 2090/0817; A61B 90/50; A61B 17/02; A61B 17/4241; A61B 2017/00212; A61B 2017/00398; A61B 2017/00477; A61B 2017/00557; A61B 2090/309; A61B 50/20; A61B 1/06; A61B 17/42; A61F 2/0009
USPC ........................ 600/37, 29, 30; 128/897–899
See application file for complete search history.

(56) References Cited

U.S. PATENT DOCUMENTS

| | | | | | |
|---|---|---|---|---|---|
| 1,615,728 | A | * | 1/1927 | Smith | A61D 9/02 128/834 |
| 1,653,352 | A | * | 12/1927 | Faudi | F16C 11/0619 403/122 |

(Continued)

FOREIGN PATENT DOCUMENTS

WO 2016134135 A1 8/2016

OTHER PUBLICATIONS

International Search Report and Written Opinion for PCT Application No. PCT/US2016/53941, dated Nov. 14, 2016, 16 pages.

*Primary Examiner* — Navin Natnithithadha
*Assistant Examiner* — Sunita Reddy
(74) *Attorney, Agent, or Firm* — Brake Hughes Bellermann LLP (57) ABSTRACT

According to an aspect, a medical device includes a base member and an adjustment member. The adjustment member is movably coupled to the base member. The adjustment member has a body portion and a coupling portion. The coupling portion is configured to couple a medical tool to the adjustment member.

14 Claims, 7 Drawing Sheets

(51) Int. Cl.
*A61B 1/06* (2006.01)
*A61F 2/00* (2006.01)
*A61B 50/20* (2016.01)
*A61B 90/00* (2016.01)
A61B 17/00 (2006.01)
A61B 90/30 (2016.01)
A61B 17/02 (2006.01)
A61B 17/30 (2006.01)

(56) References Cited

U.S. PATENT DOCUMENTS

| | | | | |
|---|---|---|---|---|
| 3,216,754 | A * | 11/1965 | Smith | F16C 11/0633 403/140 |
| 3,253,330 | A * | 5/1966 | Davies | F16C 11/0623 29/441.1 |
| 3,253,845 | A * | 5/1966 | Davies | F16C 11/0623 29/441.1 |
| 3,423,115 | A * | 1/1969 | Korecky | F16C 11/0633 403/140 |
| 3,580,313 | A * | 5/1971 | McKnight | A61B 17/10 606/75 |
| 3,669,118 | A | 6/1972 | Miguel et al. | |
| 4,241,912 | A * | 12/1980 | Mercer | A63B 23/20 482/91 |
| 4,747,393 | A * | 5/1988 | Medwid | A61B 17/0493 600/201 |
| 4,881,526 | A * | 11/1989 | Johnson | A61H 19/44 601/15 |
| 5,217,463 | A * | 6/1993 | Michael | A61B 17/02 606/53 |
| 5,483,832 | A * | 1/1996 | Pauser | A61B 5/227 600/591 |
| 5,518,503 | A * | 5/1996 | Rooney | A61B 13/00 600/240 |
| 5,520,703 | A * | 5/1996 | Essig | A61B 17/0469 606/144 |
| 5,785,640 | A * | 7/1998 | Kresch | A61F 2/005 600/29 |
| 6,048,351 | A * | 4/2000 | Gordon | A61B 17/0469 112/169 |
| 6,068,591 | A * | 5/2000 | Bruckner | A61B 17/064 600/30 |
| 6,165,108 | A * | 12/2000 | Ralston | A63B 23/20 482/105 |
| 6,264,676 | B1 * | 7/2001 | Gellman | A61B 17/0401 600/29 |
| 6,394,939 | B1 * | 5/2002 | Stein | A63B 21/026 482/148 |
| 7,001,317 | B2 * | 2/2006 | Marcotte | A63B 23/20 128/833 |
| 7,037,255 | B2 * | 5/2006 | Inman | A61B 17/0401 600/30 |
| 7,048,682 | B2 * | 5/2006 | Neisz | A61B 17/0401 600/30 |
| 7,371,245 | B2 * | 5/2008 | Evans | A61B 17/06066 606/151 |
| 7,611,454 | B2 * | 11/2009 | De Leval | A61B 17/0469 600/30 |
| 7,981,024 | B2 * | 7/2011 | Levy | A61B 17/42 600/37 |
| 8,960,622 | B2 | 2/2015 | Von Pechmann et al. | |
| 2001/0018597 | A1 | 8/2001 | Gellman et al. | |
| 2002/0000233 | A1 * | 1/2002 | Jude | A63B 23/20 128/897 |
| 2002/0028980 | A1 * | 3/2002 | Thierfelder | A61B 17/00234 600/37 |
| 2002/0116025 | A1 * | 8/2002 | Haab | A61B 5/202 606/206 |
| 2005/0000523 | A1 * | 1/2005 | Beraud | A61B 17/06004 128/885 |
| 2005/0131393 | A1 * | 6/2005 | Chu | A61B 17/00234 606/1 |
| 2005/0256530 | A1 * | 11/2005 | Petros | A61B 17/0401 606/151 |
| 2005/0277948 | A1 * | 12/2005 | Cedars | A61B 17/42 606/119 |
| 2005/0278037 | A1 * | 12/2005 | Delorme | A61F 2/0045 623/23.72 |
| 2006/0058578 | A1 * | 3/2006 | Browning | A61B 17/0401 600/37 |
| 2006/0089525 | A1 * | 4/2006 | Mamo | A61B 17/0401 600/37 |
| 2006/0195007 | A1 * | 8/2006 | Anderson | A61B 17/0401 600/29 |
| 2006/0217589 | A1 * | 9/2006 | Wan | A61B 17/0482 600/29 |
| 2006/0229596 | A1 * | 10/2006 | Weiser | A61B 17/00234 606/37 |
| 2007/0015953 | A1 * | 1/2007 | MacLean | A61B 17/06066 600/31 |
| 2007/0018958 | A1 * | 1/2007 | Tavakoli | B25J 3/04 345/161 |
| 2008/0039678 | A1 * | 2/2008 | Montpetit | A61B 17/06109 600/30 |
| 2010/0137692 | A1 * | 6/2010 | Lindsay | A61B 17/02 600/235 |
| 2010/0268014 | A1 * | 10/2010 | Pitman | A61N 5/1049 600/7 |
| 2010/0312051 | A1 * | 12/2010 | Brown | A61B 17/0401 600/37 |
| 2012/0016185 | A1 * | 1/2012 | Sherts | A61B 17/12099 600/37 |
| 2013/0005543 | A1 * | 1/2013 | Armitage | A63B 23/20 482/131 |
| 2013/0035543 | A1 * | 2/2013 | Fischer | A61F 2/0045 600/37 |
| 2013/0197537 | A1 | 8/2013 | Fairneny et al. | |
| 2015/0133958 | A1 | 5/2015 | Singh et al. | |
| 2015/0148812 | A1 | 5/2015 | Ahluwalia | |
| 2017/0319871 | A1 * | 11/2017 | Pitman | A61N 5/1049 |

* cited by examiner

SURGICAL TOOL CONTROL DEVICES AND METHODS OF USING THE SAME

CROSS-REFERENCE TO RELATED APPLICATION

This application is a Nonprovisional of, and claims priority to, U.S. Patent Application No. 62/234,974, filed on Sep. 30, 2015, entitled "SURGICAL TOOL CONTROL DEVICES AND METHODS OF USING THE SAME", which is incorporated by reference herein in its entirety.

TECHNICAL FIELD

This disclosure relates generally to medical devices and more particularly to medical devices that are configured to control or support surgical tools.

BACKGROUND

A variety of medical procedures are performed to repair portions of a body of a patient. For example, some medical procedures are performed to repair or provide support to portions, such as organs, of the body of the patient. Specifically, in some medical procedures are performed to repair pelvic organ prolapse. Sacralcolpopexy is one example of such a procedure.

During some medical procedures, it may be desirable or required to move or otherwise manipulate a portion of the body of the patient. For example, during a sacralcolpopexy, which may be performed using an open abdominal technique or a minimally invasive technique, a vaginal manipulator or a probe may be used to move or manipulate the vagina. For example, a physician may move the vagina around to provide access to the anterior or posterior portions of the vagina.

Some of the medical procedures that are performed to repair portions of the body of the patient are time consuming. For example, for a sacralcolpopexy, dissection may take up to 45 minutes. It may take up to an additional 45 minutes to place or fix the mesh to the vagina of the patient. During such time, the physician or the physician assistant may become tired from holding or supporting the vaginal manipulator or probe that is being used to facilitate the procedure.

Accordingly, is may be desirable to provide a device that includes components or features that might facilitate the performance of medical procedures. For example, it may be desirable to provide a device that includes components or features that might facilitate the holding or retaining of a medical tool or instrument during medical procedures.

SUMMARY

According to an aspect, a medical device includes a base member and an adjustment member. The adjustment member is movably coupled to the base member. The adjustment member has a body portion and a coupling portion. The coupling portion is configured to couple a medical tool to the adjustment member. At least a portion of the medical tool is configured to be inserted into a vagina of a patient.

In some embodiments, the base member is configured to be disposed proximate the patient during a sacrocolpopexy procedure.

In some embodiments, the adjustment member is slidably coupled to the base member. In some embodiments, the adjustment member is slideably and rotatably coupled to the base member.

In some embodiments, the coupling portion is configured to move with respect to the body portion. In some embodiments, the coupling portion of the adjustment member is slidably coupled to the body portion of the adjustment member.

In some embodiments, the base member is configured to be removably coupled to a surface of an operating table. In some embodiments, the base member has an upper surface and a lower surface opposite the upper surface, the lower surface being configured to be disposed adjacent a surface of an operating table, the adjustment member being movably coupled to the upper surface of the base member.

In some embodiments, the coupling portion of the adjustment member is configured to be slidably coupled to the medical tool. In some embodiments, the adjustment member is rotably coupled to the base.

In some embodiments, the coupling portion of the adjustment member includes a lock member, the lock member being configured to move with respect to the body of the adjustment member.

In some embodiments, the medical device includes a control device, the control device configured to remotely move the adjustment member with respect to the base member. In some embodiments, the medical device includes a wireless control device, the control device configured to remotely move the adjustment member with respect to the base member.

In some embodiments, the medical tool is removably coupled to the adjustment member. In some embodiments, the medical tool has a distal end portion, the distal end portion of the medical tool being configured to be placed in a first configuration and a second configuration. In some embodiments, the medical tool is configured to be placed in a first configuration and a second configuration, the medical tool having a first size when the medical tool is in the first configuration and having a second size when the medical tool is in the second configuration, the first size being smaller than the second size.

According to an aspect, a medical device includes a base member, an adjustment member, and a adjustment member, and a medical tool. The adjustment member is movably coupled to the base member. The adjustment member has a body portion and a coupling portion. The medical tool is movably coupled to the adjustment member. At least a portion of the medical tool is configured to be inserted into a vagina of a patient.

In some embodiments, the medical tool is removably coupled to the adjustment member. In some embodiments, the adjustment member is slideably and rotatably coupled to the base member.

In some embodiments, the coupling portion of the adjustment member is configured to move with respect to the body portion of the adjustment member. In some embodiments, the coupling portion of the adjustment member is slidably coupled to the body portion of the adjustment member.

In some embodiments, the base member is configured to be removably coupled to a surface of an operating table. In some embodiments, the base member has an upper surface and a lower surface opposite the upper surface, the lower surface being configured to be disposed adjacent a surface of an operating table, the adjustment member being movably coupled to the upper surface of the base member.

According to an aspect, a method includes placing a medical device near a patient, the medical device having a base member and an adjustable member; moving the adjustable member with respect to the base member; and inserting a medical tool coupled to the adjustable member into a vagina of a patient.

In some embodiments, the moving the adjustable member with respect to the base member includes sliding the adjustable member with respect to the base member.

In some embodiments, the method includes moving the medical tool with respect to the adjustable member.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
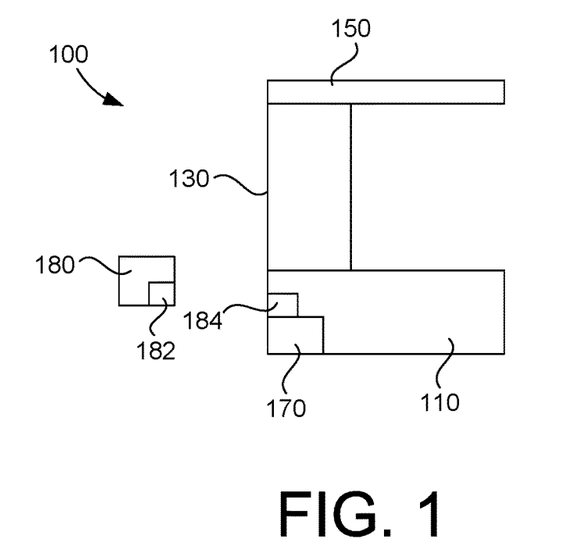
FIG. 1 is a schematic illustration of a medical device according to an embodiment.

FIG. 1 is a schematic illustration of a medical device 100 according to an embodiment of the invention. The medical device 100 may be used in surgical procedures. For example, in some embodiments, the medical device 100 may be disposed such that a portion of the medical device 100 is disposed within a portion of a body of a patient during a surgical procedure. Specifically, in some cases, the medical device 100 may be used to support or manipulate a portion of the body of the patient during the surgical procedure (to help facilitate the surgical procedure). In one embodiment, the medical device 100 may be used during a surgical procedure in the pelvic region of the patient (such as a sacrocolpopexy). The medical device 100 may be placed such that a portion of the device 100 is disposed within the vagina of the patient. The medical device 100 may then be used to support and or move or manipulate the vagina of the patient during the surgical procedure.

In the illustrated embodiment, the medical device 100 includes a base member 110 and an adjustment member 130. The adjustment member 130 is configured to move with respect to the base member 110. The adjustment member 130 is movably coupled to the base member 110.

In some embodiments, the adjustment member 130 is slidably coupled to the base member 110. In some embodiments, the adjustment member 130 is slidably coupled to the base member 110 such that it can slide with respect to the base member 110 in two directions (a first direction and a second direction opposite the first direction). In other embodiments, the adjustment member 130 is slidably coupled to the base member 110 such that it can move or slide with respect to the base member 110 in more than two directions, such as 4 or more directions.

In some embodiments, the adjustment member 130 is rotatably coupled to the base member 110. In some embodiments, the adjustment member 130 is rotatably and slidably coupled to the base member 110. In such embodiments, the adjustment member 130 is configured to slide and rotate with respect to the base member 110.

In other embodiments, the adjustment member 130 is configured to be coupled to the base member 110 at a plurality of locations on the base member 110. For example, in some embodiments, the adjustment member 130 is configured to be removably coupled to the base member 110 at a first location on the base member 110 and at a second location on the base member 110 different than the first location.

The adjustment member 130 is configured to be coupled to a medical tool 150. In some embodiments, the adjustment member 130 includes a coupling portion and a body portion. In such embodiments, the coupling portion is configured to receive or be coupled to the medical tool 150. In some embodiments, the coupling portion of the adjustment member 130 is configured to move with respect to the body portion of the adjustment member 130. For example, in some embodiments, the coupling portion is configured to slide and/or pivot with respect to the body portion. In such embodiments, the medical tool 150 may be slid and/or pivoted with respect to the body member.

In some embodiments, the medical tool 150 is coupled to or received by the adjustment member 130 such that the medical tool 150 may be moved with respect to the adjustment member 130. For example, in some embodiments, the medical tool 150 is slidably coupled to the coupling portion of the adjustment member 130. In such embodiments, the medical tool 150 may be slid or otherwise moved with respect to the coupling portion.

The medical tool 150 may be of any shape or size. In some embodiments, the medical tool 150 includes a distal end portion that is configured to be disposed within a body of a patient to move, manipulate, or provide support to a portion of a body of a patient. For example, in some embodiments, the medical tool 150 may be configured to be disposed within a body of a patient to move, manipulate, or provide support to a portion of a body of a patient during a medical surgery or procedure. In some embodiments, the medical tool 150 is a vaginal manipulator and includes a distal end portion that is configured to be inserted into a vagina of a patient. In such embodiments, the medical tool 150 is configured to move, manipulate, or support the vagina of the patient during a surgical procedure, such as a sacrocolcopexy.

In some embodiments, the medical tool 150 may be configured to be placed in a first configuration and a second configuration different than the first configuration. For example, in some embodiments, the medical tool 150 may be configured such that a portion (such as the distal end portion of the medical tool 150) may be placed in small or contracted configuration and in a larger or expanded configuration. In such embodiments, the medical tool 150 may be placed in its small or contracted configuration and inserted into the body of the patient. Once disposed within the body of the patient, the distal end portion of the medical tool 150 may then be placed in its larger or expanded configuration.

In some embodiments, the medical device 100 is configured to move the various portions or members of the device 100 with respect to each other. For example, in some embodiments, the medical device 100 includes a motor 170. The motor 170 may be operatively coupled to the various portions or members of the device 100 to move such members with respect to each other. In some embodiments, the motor 170 may be operatively coupled to the various portions or members of the device to maintain or retain the various portions or members of the device in their set or desired potions with respect to each other.

For example, in some embodiments, the motor 170 is operatively coupled to the adjustment member 130 and is configured to move (such as slide and/or rotate) the adjustment member 130 with respect to the base member 110. In some embodiments, the motor 170 is operatively coupled to the coupling portion of the adjustment member 130 and is configured to move the coupling portion of the adjustment member 130 with respect to the body member of the adjustment member 130.

In some embodiments, the medical device 100 may be controlled or moved remotely. For example, in some embodiments, the various portions or members of the medical device 100 may be moved with respect to each other from a location remote from the device 100 itself. In some embodiments, the medical device 100 includes a remote control device 180. The remote control device 180 may be operatively coupled to the medical device 100 such that the remote control device 180 may be used to control or move the various portion or members of the device 100 with respect to each other. In some embodiments, the remote control device 180 is a wired to the medical device 100. In other embodiments, the remote control device 180 is configured to wirelessly control the medical device 100. In such embodiments, the remote control device 180 may include a transmitter 182 that is configured to communicate with a receiver 184 of the medical device 100. In some embodiments, the remote control device 180 is voice activated. In such embodiments, the remote control device 180 includes a sound or voice receiver (such as a microphone) and is configured to communicate with the receiver 184 of the medical device 100 based on the sounds or voice commands received by the remote control device 180.

In some embodiments, the remote control device 180 is configured to communicate with and operate or activate features of the medical tool 150. For example, in some embodiments, the remote control device 180 is configured to actuate or cause a portion of the medical tool 150 to expand. In other embodiments, the remote control device 180 is configured to actuate or cause a light source of the medical tool 150 to turn on or to turn off In use, the medical device 100 may be placed on an operating surface. For example, in some embodiments, the medical device 100 may be placed on a surface, such as an upper or top surface of an operating table. In some embodiments, the medical device 100 is configured to be coupled to the surface of the operating table. For example, in some embodiments, the medical device 100 includes couplers, magnets, or other devices or members that are configured to removably couple the medical device to an operating surface. In other embodiments, the medical device 100 includes a clamp or clamp member that is configured to couple the medical device 100 to the operating table. In another embodiment, a portion of the medical device 100 may be disposed between the body of the patient and the operating table. In such embodiments, the weight of the patient may help retain the medical device 100 in place on the operating table.

A portion of the medical device may be inserted into a body of the patient. For example, in some embodiments, a distal end portion of the medical tool 150 may be inserted into a body of the patient. Specifically, during a sacrocolpopexy procedure, a portion of the medical tool 150 may be inserted into a vagina of the patient.

The medical device 100 may then be moved or adjusted to appropriately move, manipulate or support the portion of the body of the patient. For example, in some embodiments, the adjustment member 130 may be moved with respect to the base member 110 to move the medical tool 150 (or the position of the medical tool 150) within the body of the patient.

In some embodiments, the medical device 100 may be moved or adjusted during the medical procedure. For example, in some embodiments, the portion of the body being moved, manipulated or supported may need to be placed or supported at a first position or orientation during a first portion of the surgical procedure and may need to be placed or supported at a second position or orientation during a second portion of the surgical procedure.

In some embodiments, once the surgical procedure is complete, the medical device 100 may be removed from the body of the patient. In some embodiments, the medical device 100 may also be removed from the operating surface or table.

Figure 2:
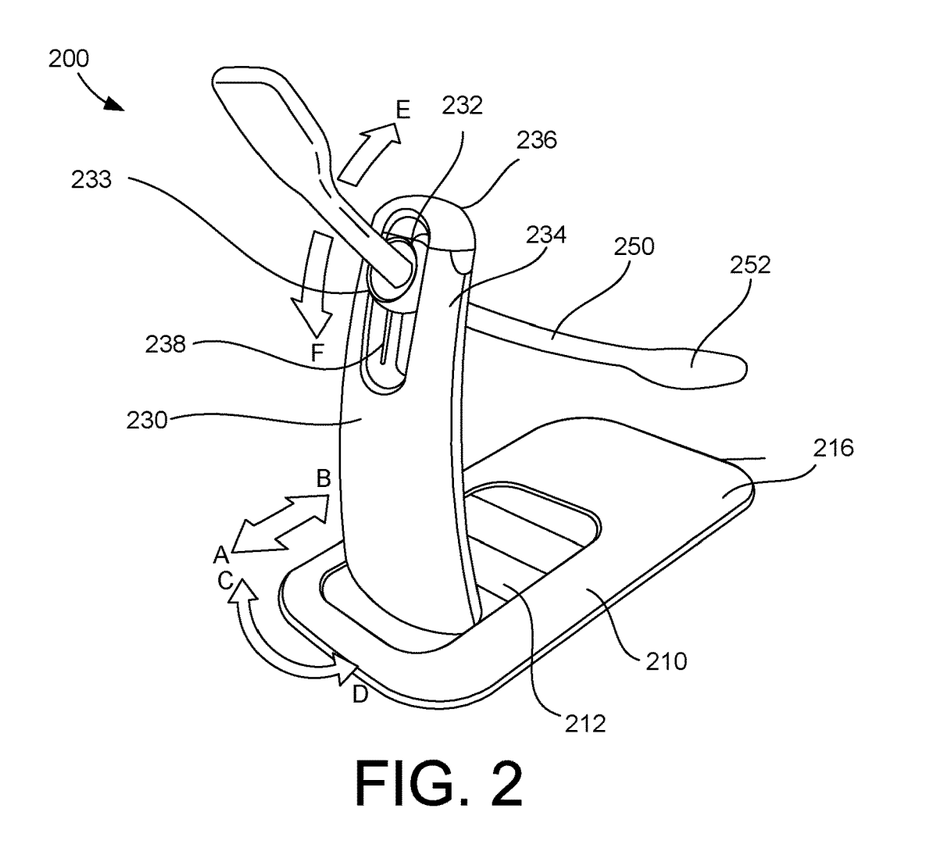
FIGS. 2 and 3 are perspective views of a medical device according to an embodiment.
Figure 3:
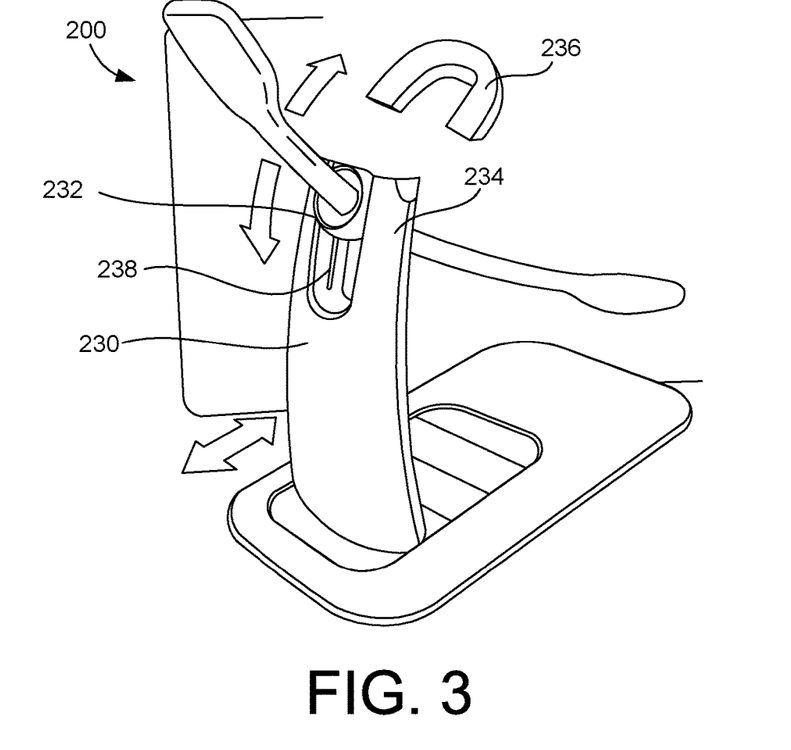

FIGS. 2 and 3 are perspective views of a medical device 200 according to an embodiment. The medical device 200 may be used in surgical procedures. For example, in some embodiments, the medical device 200 may be disposed such that a portion of the medical device 200 is disposed within a portion of a body of a patient during a surgical procedure. Specifically, in some cases, the medical device 200 may be used to support or manipulate a portion of the body of the patient during the surgical procedure (to help facilitate the surgical procedure). In one embodiment, the medical device 200 may be used during a surgical procedure in the pelvic region of the patient (such as a sacrocolpopexy). The medical device 200 may be placed such that a portion of the device 200 is disposed within the vagina of the patient. The medical device 200 may then be used to support and or move or manipulate the vagina of the patient during the surgical procedure.

In the illustrated embodiment, the medical device 200 includes a base member 210 and an adjustment member 230. The adjustment member 230 is configured to move with respect to the base member 210. The adjustment member 230 is movably coupled to the base member 210.

In the illustrated embodiment, the adjustment member 230 is slidably coupled to the base member 210. Specifically, the adjustment member 230 is slidably coupled to the base member 210 such that it can slide with respect to the base member 210 in two directions. The adjustment member 230 is configured to move with respect to the base member 210 in a first direction (direction of arrow A) and in a second direction (the direction of arrow B) opposite the first direction. In the illustrated embodiment, the adjustment member 230 is coupled to and configured to slide within a channel 212 defined by the base member 210. In other embodiments, the adjustable member 230 is movably coupled to the base member 210 via a different sliding or moving mechanism.

In other embodiments, the adjustment member 230 is slidably coupled to the base member 210 such that it can move or slide with respect to the base member 210 in more than two directions, such as 4 or more directions.

In the illustrated embodiment, the adjustment member 230 is rotatably coupled to the base member 210. The adjustment member 230 may rotate about an axis in a first direction (the direction of arrow C) and in a second direction (the direction of arrow D). In some embodiments, the adjustment member 230 or a portion of the adjustment member 230 is coupled to the base member 210 via a post or pin such that the adjustment member 230 may rotate about such coupling member. Accordingly, the adjustment member 230 is configured to slide and rotate with respect to the base member 210.

In other embodiments, the adjustment member 230 is configured to be coupled to the base member 210 at a plurality of locations on the base member 210. For example, in some embodiments, the adjustment member 230 is configured to be removably coupled to the base member 210 at a first location on the base member 210 and at a second location on the base member 210 different than the first location.

In the illustrated embodiment, the base member 210 includes an upper portion or surface 216 and a lower portion or surface 214. The upper portion or surface 216 is disposed opposite the lower portion or surface 214. In the illustrated embodiment, the adjustment member 230 is slidably coupled to the upper portion or surface 216. The lower portion or surface 214 is configured to be disposed on or adjacent an operating surface (as described in more detail below).

The adjustment member 230 is configured to be coupled to a medical tool 250. In the illustrated embodiment, the adjustment member 230 includes a coupling portion 232 and a body portion 234. The coupling portion 232 is configured to receive or be coupled to the medical tool 250.

In the illustrated embodiment, the adjustment member 230 includes a lock member 236. The lock member 236 is configured to be movably coupled to the body portion 234 of the adjustment member 230. In the illustrated embodiment (as best illustrated in FIG. 3), the lock member 236 may be removably coupled to the body portion 234. For example, the lock member 236 may be snap fit or frictionally fit to the body portion 234. In other embodiments, the lock member 236 is rotatably, pivotally, or otherwise movably coupled to the body portion 234 of the adjustment member 230.

In the illustrated embodiment, the lock member 236 may be removed from the body portion 234 of the adjustment member 230 to an unlock state or configuration to allow the insertion or coupling of the medical tool 250 to the coupling portion 232 of the adjustment member 230. The lock member 236 may then be coupled to the body portion 234 (a locked state or configuration) to lock the medical tool 250 to the coupling portion 232.

The coupling portion 232 of the adjustment member 230 is configured to move with respect to the body portion 234 of the adjustment member 230. In the illustrated embodiment, the coupling portion 232 is configured to slide with respect to the body portion 234. Specifically, the coupling portion 232 is configured to slide within a track 238 that is defined by the body portion 234 of the adjustment member 230. Accordingly, the medical tool 250 may be slid with respect to the body portion 234 in a first direction (in the direction of arrow E) and in a second direction (in the direction of arrow F).

In the illustrated embodiment, the coupling portion 232 is configured to rotate and pivot with respect to the body portion 234 of the adjustment member 230. Thus, in the illustrated embodiment, the coupling portion 232 and the medical tool 250 may be pivoted and rotated.

In the illustrated embodiment, the coupling portion 232 is configured to be placed in a position with respect to the body portion 234 of the adjustment member 230. Specifically, the coupling portion 232 is configured to be moved or placed in a position such that the coupling portion 232 holds or retains the medical tool 250 in a fixed position. In the illustrated embodiment, the coupling portion 232 includes a gimbal or retention member 233. The gimbal or retention member 233 is configured to hold or maintain the setting or position of the coupling portion 232 and the medical tool 250 with respect to the body portion 234. In some embodiments, the gimbal or retention member is a frictional gimbal or lock member and is configured to, via friction, hold or retain the coupling portion 232 and the medical tool 250 in place or position. In other embodiments, the gimbal may include a lever or a cam that may be actively moved and used to lock the medical tool 250 in place or position.

In the illustrated embodiment, the medical tool 250 is coupled to or received by the adjustment member 230 such that the medical tool 250 may be moved with respect to the adjustment member 230. For example, in the illustrated embodiment, the medical tool 150 is frictionally coupled to the coupling portion 232 and may be slid or otherwise moved with respect to the coupling portion 232. In some embodiments, the medical tool 250 is configured for a single use and is disposable. In other embodiments, the medical tool 250 is reusable and is thus, configured to be used in multiple surgical procedures.

The medical tool 250 may be of any shape or size. In the illustrated embodiment, the medical tool 250 includes a distal end portion that is configured to be disposed within a body of a patient to move, manipulate, or provide support to a portion of a body of a patient. For example, in some embodiments, the medical tool 250 may be configured to be disposed within a body of a patient to move, manipulate, or provide support to a portion of a body of a patient during a medical surgery or procedure. In the illustrated embodiment, the medical tool 250 is a vaginal manipulator and includes a distal end portion 252 that is configured to be inserted into a vagina of a patient. In such embodiments, the medical tool 250 is configured to move, manipulate, or support the vagina of the patient during a surgical procedure, such as a sacrocolcopexy.

Figure 4:
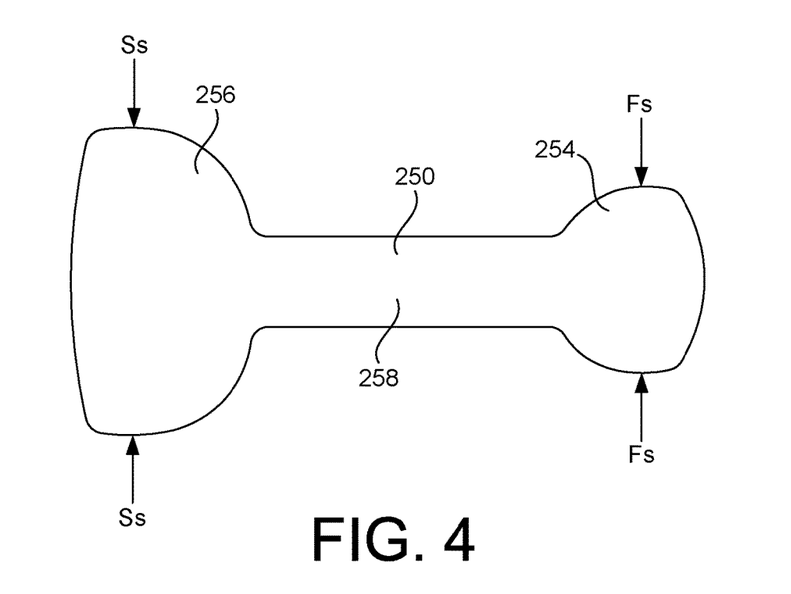
FIG. 4 is a top view of a medical tool of the medical device of FIGS. 2 and 3.

As best illustrated in FIG. 4, the medical tool 250 includes a first end portion 254 and a second end portion 256. The medical tool 250 also includes a shaft portion 258 that is disposed between the first end portion 254 and the second end portion 256. The first end portion 254 has a first size FS and the second end portion 256 has a second size SS. The first size FS is smaller than the second size SS. The medical tool 250 is configured to be coupled to or received by the adjustment member 230 such that either end portion may be inserted into the body of patient. In other words, if the medical practitioner desires to have the smaller portion of the medical tool 250 inserted into the body of the patient, the medical practitioner may insert or couple the medical tool 250 to the adjustment member 230 in a first direction or orientation. If the medical practitioner desires to have the larger portion of the medical tool 250 inserted into the body of the patient, the medical practitioner may insert or couple the medical tool 250 to the adjustment member 230 in a second or opposite direction or orientation.

Figure 5:
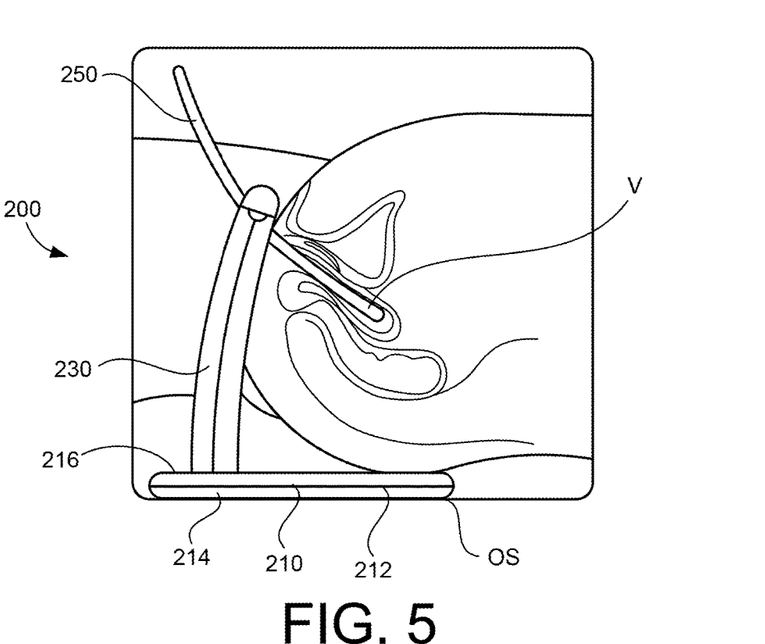
FIGS. 5 and 6 are schematic illustrations of the medical device of FIGS. 2 and 3 with a portion of the medical device disposed within a patient.
Figure 6:
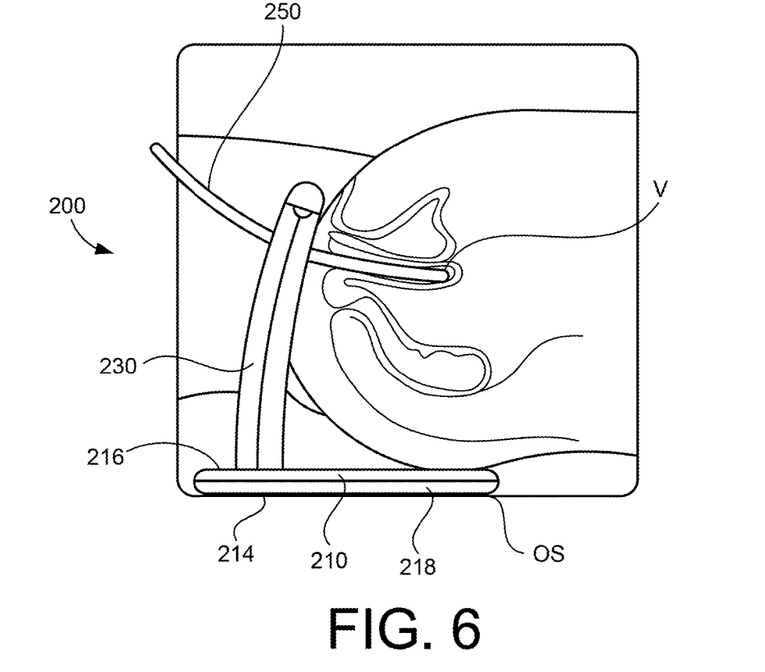

In use, the medical device 200 may be placed on an operating surface OS. For example, in some embodiments, the medical device 200 may be placed on a surface, such as an upper or top surface of an operating table. In some embodiments, the medical device 200 is configured to be coupled to the surface of the operating table. For example, in some embodiments, the medical device 200 includes couplers, magnets, or other devices or members that are configured to removably couple the medical device to the operating surface OS. As best illustrated in FIGS. 5 and 6, in the illustrated embodiment, the base member 210 includes a support portion 218. The support portion 218 is configured to be disposed below a portion of the body of the patient (such that the support portion 218 is disposed between the portion of the body of the patient and the operating surface OS). Accordingly, the body of the patient may help to secure the medical device 200 to the operating surface OS.

A portion of the medical device 200 may be inserted into a body of the patient. For example, in some embodiments, a distal end portion 252 of the medical tool 250 may be inserted into a body of the patient. Specifically, during a sacrocolpopexy procedure, a portion of the medical tool 250 may be inserted into a vagina of the patient.

The medical device 200 may then be moved or adjusted to appropriately move, manipulate or support the portion of the body of the patient. For example, in some embodiments, the adjustment member 230 may be moved with respect to the base member 210 to move the medical tool 250 (or the position of the medical tool 250) within the body of the patient.

In some embodiments, the medical device 200 may be moved or adjusted during the medical procedure. For example, in some embodiments, the portion of the body being moved, manipulated or supported may need to be placed or supported at a first position or orientation during a first portion of the surgical procedure and may need to be placed or supported at a second position or orientation during a second portion of the surgical procedure. For example, as schematically illustrated in FIG. 5, during a sacrocolpopexy procedure, the device 200 may be positioned within the vagina V of the patient such that the vagina is positioned for apical access (or access to the anterior portion of the vagina). In such an embodiment, the vagina is positioned to facilitate the coupling of a bodily implant to the anterior portion of the vagina V. As schematically illustrated in FIG. 6, during a different portion of the sacrocolpopexy procedure, the device 200 may be moved such that the vagina V of the patient is positioned for trans-apical access (or access to the posterior portion of the vagina). According, the vagina is positioned to facilitate the coupling of the bodily implant to a posterior portion of the vagina V.

In some embodiments, once the surgical procedure is complete, the medical device 200 may be removed from the body of the patient. In some embodiments, the medical device 200 may also be removed from the operating surface or table.

Figure 7:
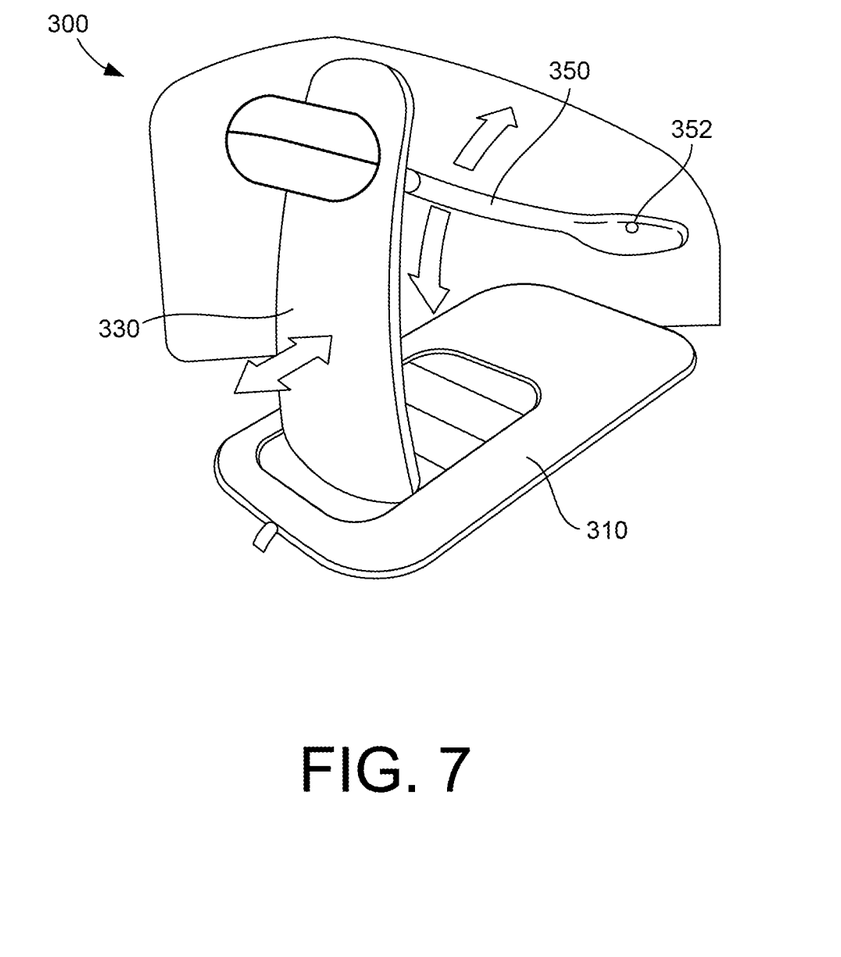
FIG. 7 is a perspective view of a medical device according to another embodiment.
Figure 8:
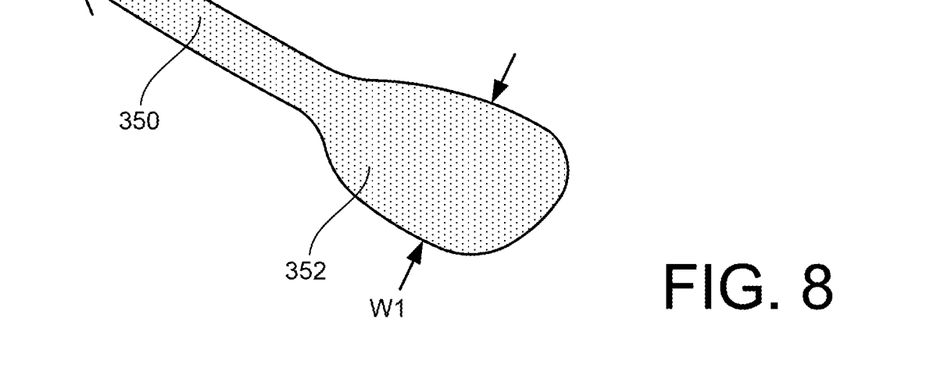
FIGS. 8 and 9 are top views of a portion of a medical tool of the medical device of FIG. 7.
Figure 9:
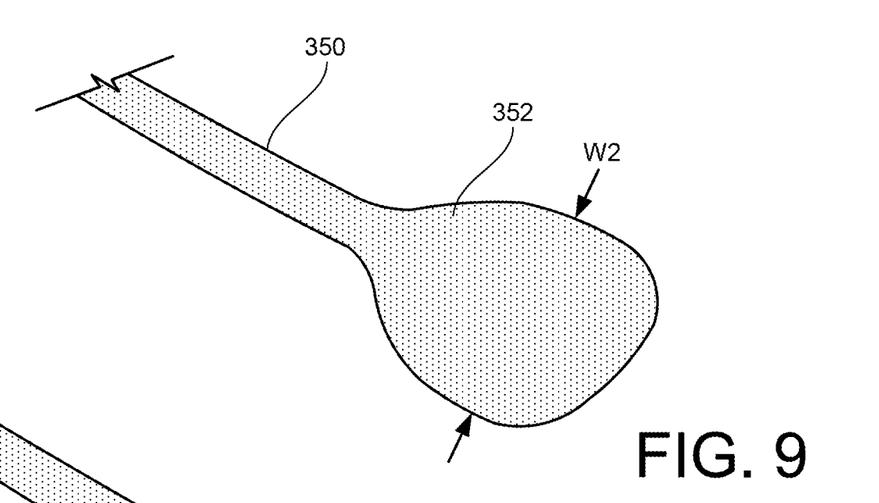
Figure 12:
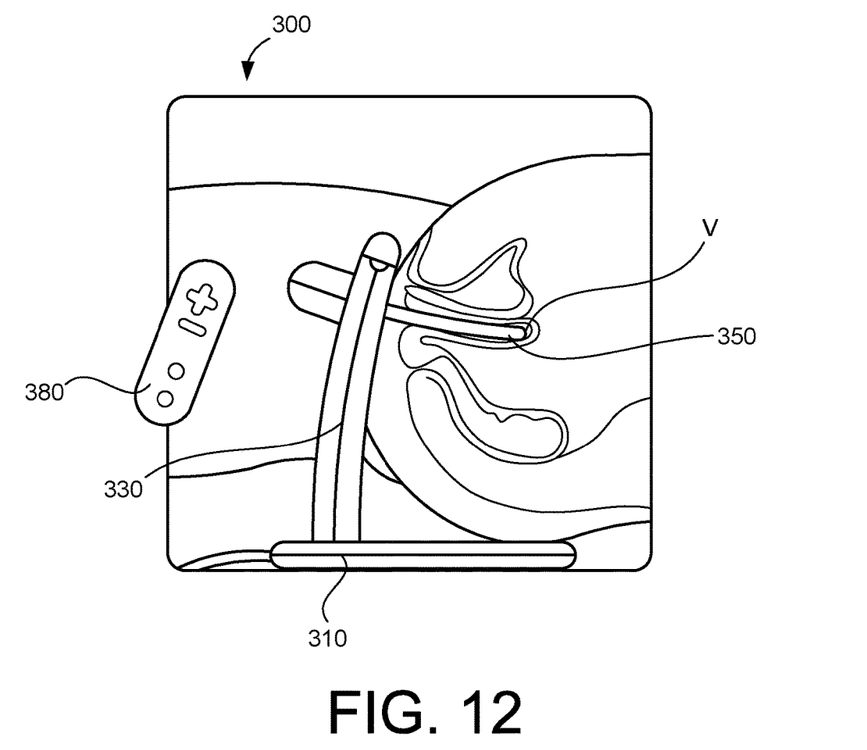
FIG. 12 is a schematic illustration of the medical device of FIG. 7 with a portion of the medical device disposed within a patient.

FIG. 7 is a perspective view of a medical device 300 according to an embodiment. FIGS. 8 and 9 are top views of a portion of a medical tool 350 of the medical device 300. FIG. 12 is a schematic illustration of the medical device 300 disposed within a portion of a body of a patient.

The medical device 300 may be used in surgical procedures. For example, in some embodiments, the medical device 300 may be disposed such that a portion of the medical device 300 is disposed within a portion of a body of a patient during a surgical procedure. Specifically, in some cases, the medical device 300 may be used to support or manipulate a portion of the body of the patient during the surgical procedure (to help facilitate the surgical procedure). In one embodiment, the medical device 300 may be used during a surgical procedure in the pelvic region of the patient (such as a sacrocolpopexy). The medical device 300 may be placed such that a portion of the device 300 is disposed within the vagina of the patient. The medical device 300 may then be used to support and or move or manipulate the vagina of the patient during the surgical procedure.

In the illustrated embodiment, the medical device 300 includes a base member 310 and an adjustment member 330. The adjustment member 330 is configured to move with respect to the base member 310. In the illustrated embodiment, the adjustment member 330 is movably coupled to the base member 310.

The adjustment member 330 is configured to be coupled to the medical tool 350. The medical tool 350 is configured to move with respect to the adjustment member 330. For example, in some embodiment, the medical tool 350 is configured to slide and/or pivot or rotate with respect to the adjustment member 330. In some embodiments, the medical tool 350 is a single use tool (to be used on a single patient and disposed after the use). In such embodiments, the medical tool 350 may be removably coupled to the adjustment member 330.

Figure 10:
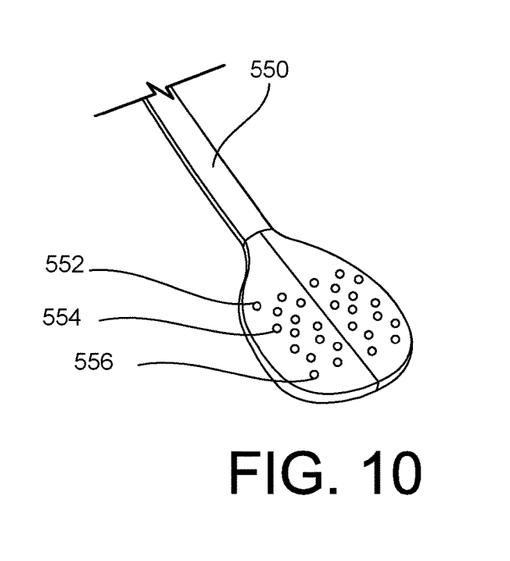
FIGS. 10 and 11 are top views of a portion of a medical tool according to an embodiment.

The medical tool 350 may be of any shape or size. In the illustrated embodiment, the medical tool 350 includes a distal end portion that is configured to be disposed within a body of a patient to move, manipulate, or provide support to a portion of a body of a patient. For example, in some embodiments, the medical tool 350 may be configured to be disposed within a body of a patient to move, manipulate, or provide support to a portion of a body of a patient during a medical surgery or procedure. In the illustrated embodiment (as best illustrated in FIG. 10), the medical tool 350 is a vaginal manipulator and includes a distal end portion 352 that is configured to be inserted into a vagina V of a patient. In such embodiments, the medical tool 350 is configured to move, manipulate, or support the vagina of the patient during a surgical procedure, such as a sacrocolcopexy.

In the illustrated embodiment, the distal end portion 352 of the medical tool 350 is configured to expand or change shapes. For example, in one embodiment, the medical tool 350 may be inserted into a body of a patient when the distal end portion 352 of the medical tool 350 is disposed in a small or contracted configuration (as illustrated in FIG. 8). In this configuration, the distal end 352 has a size or width W1. Insertion of the medical tool 350 into the body of the patient may be facilitated with the distal end portion 352 in its small or contracted configuration. Once the distal end portion 352 is appropriately disposed within the body of the patient, the distal end portion 352 may be placed in its large or expanded configuration (as best illustrated in FIG. 9). In this configuration, the distal end 352 has a size or width W2. In this configuration, the distal end portion 352 may more easily move, manipulate, support, or stretch the desired portion of the body of the patient.

In some embodiments, the medical tool 350 is inflatable. In such embodiments, the medical tool 350 may be deflated when in its collapsed or small state or configuration and may be inflated (with a fluid such as air, water, or saline) to move to its expanded or large state or configuration. In other embodiments, another method is used to allow the medical tool 350 to move from its first or small configuration to its second or larger configuration. For example, the medical tool 350 may be formed of a material that may be stretched to assume its second or larger configuration and a mechanical structure such as linages or ribs may be mechanically moved to move the medical tool 350 from its first or small configuration to its second or larger configuration.

The medical device 300 is configured to move the various portions or members of the device 300 with respect to each other. For example, in some embodiments, the medical device 300 includes a motor. The motor may be operatively coupled to the various portions or members of the device 300 to move such members with respect to each other. In some embodiments, the motor and electronics may be operatively coupled to the various portions or members of the device to maintain or retain the various portions or members of the device in their set or desired potions with respect to each other.

For example, in some embodiments, the motor is operatively coupled to the adjustment member 330 and is configured to move (such as move in and out, slide up and down, and/or rotate) the adjustment member 330 with respect to the base member 310. In some embodiments, the motor is disposed at a distal end portion of the medical tool 350 and is operatively coupled to the coupling portion of the adjustment member 330 and is configured to move the coupling portion of the adjustment member 330 with respect to the body member of the adjustment member 330. Additionally, in some embodiments, the motor is operatively coupled to the medical tool 350. In such embodiments, the motor may be configured to move the distal end 352 of the medical tool 350 from its first configuration to its second configuration.

In some embodiments, the medical device 300 may be controlled or moved remotely. For example, in some embodiments, the various portions or members of the medical device 300 may be moved with respect to each other from a location remote from the device 300 itself. In the illustrated embodiment, the medical device 300 includes a remote control device 380. The remote control device 380 may be operatively coupled to the medical device 300 such that the remote control device 380 may be used to control or move the various portion or members of the device 300 with respect to each other. For example, in some embodiments, the remote control device 380 is configured to move the medical tool 350 up and down, slide the medical tool 350 in and out, and rotate the medical tool 350. In some embodiments, the remote control device 380 is also configured to operate features of the medical tool 350. For example, in some embodiments, the remote control device 380 is configured to move the medical tool 350 from its first or contracted position to its second or expanded configuration and vice versa. In some embodiments, the remote control device 380 is configured to activate a light source of the medical tool 350.

In some embodiments, the remote control device 380 is wired to the medical device 300. In other embodiments, the remote control device 380 configured to wirelessly control the medical device 300. In such embodiments, the remote control device 380 may include a transmitter that is configured to communicate with a receiver of the medical device 300. In some embodiment, the remote control 380 may include a graphical user interface. In other embodiments, the remote control 380 may include a series of buttons or actuators. In some embodiments, the remote control 380 may be voice activated. In such embodiments, the remote control 380 is configured to receive voice commands (such as from the physician) and control the medical device 300 appropriately.

Figure 11:
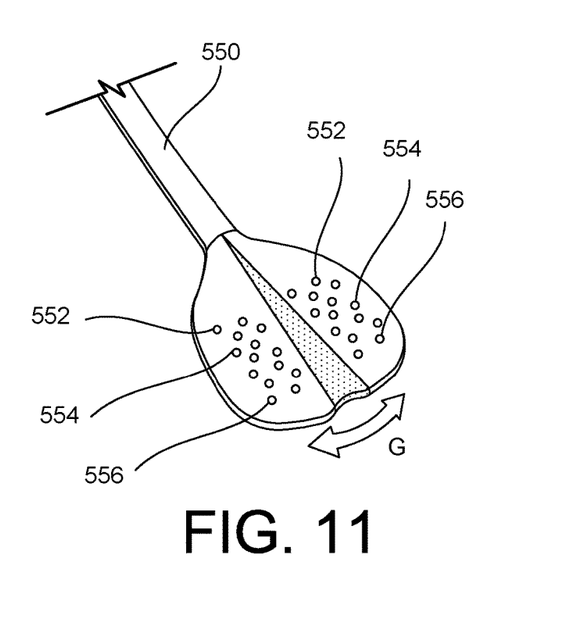

FIGS. 10 and 11 are top views of a medical tool 550 according to an embodiment of the invention. The medical tool 550 is configured to be operatively coupled to and used with a device as described above. FIG. 10 shows the medical tool 550 in a first or contracted state or configuration. FIG. 11 shows the medical tool 550 in a second or expanded state or configuration. The medical tool 550 may be inflated or otherwise mechanically expanded to assume its second or expanded state or configuration (as shown by arrow G).

In the illustrated embodiment, the medical tool 550 includes light sources 554. The light sources 554 may be activated when the medical tool 550 is disposed within the body of a patient. The light sources 554 may help illuminate the bodily tissue to help facilitate the suturing of the bodily tissue by the medical practitioner. In some embodiments, the lights sources 554 are light emitting diodes. In other embodiments, the light sources 554 or another type of light source.

In the illustrated embodiment, the medical tool 550 includes raised bumps 552. The raised bumps 552 may elevate bodily tissue disposed near the medical tool 550 to help or assist in the suturing of the bodily tissue. For example, in some embodiments, the raised bumps may help elevate vaginal tissue or tissue proximal the vagina when the medical tool 550 is disposed within a vagina of a patient.

In the illustrated embodiment, the medical tool 550 includes vacuum ports or openings 556. In some embodiments, the vacuum ports 556 may be operatively coupled to a vacuum source. The vacuum ports 556 may then pull or move tissue towards the ports 556 or surface of the medical tool 550 to help position the tool within the body of the patient or to help facilitate the suturing of the bodily tissue.

Figure 13:
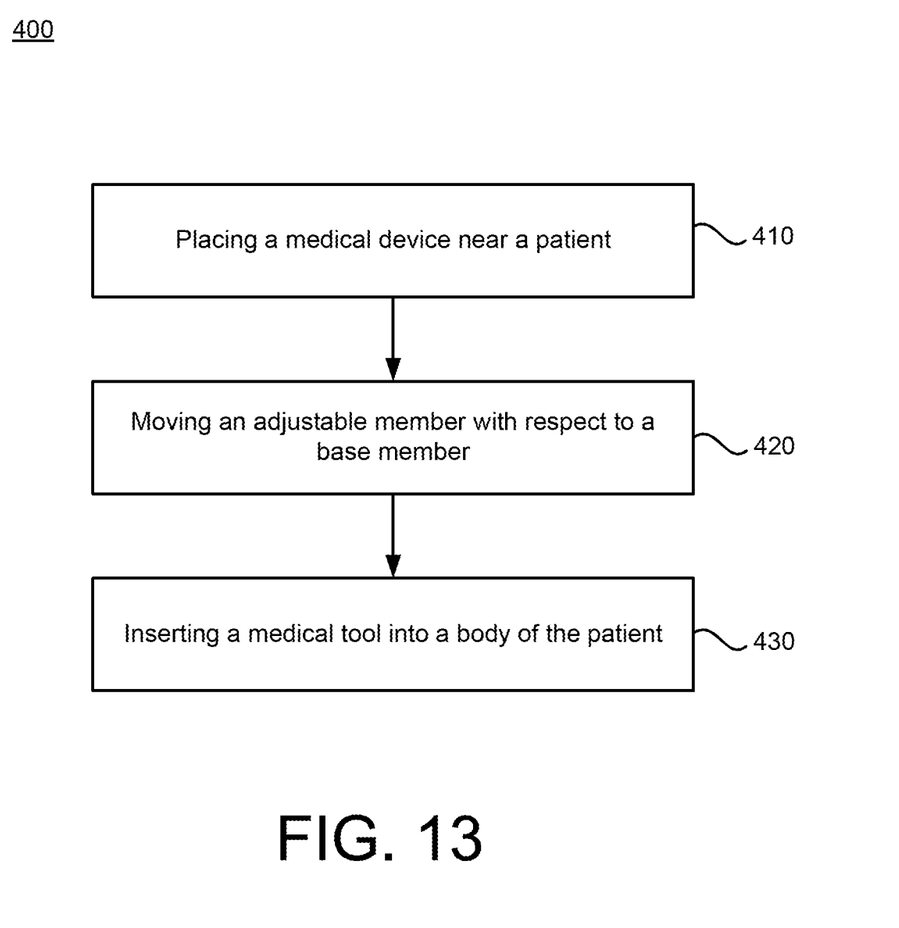
FIG. 13 is a flow chart of a method according to an embodiment.

FIG. 13 is a flow chart for a method 400 according to an embodiment. The method 400 includes at 410 placing a medical device near a patient. The medical device may include a base member and an adjustable member. In some embodiments, the placing of the medical device near or proximate the patient includes coupling the medical device to an operating surface, such as the operating table. In some embodiments, the medical device is clamped to the operating table. In other embodiments, another device, such as couplers, magnets, or adhesives are used to couple the medical device to the operating table. In some embodiments, a support portion of the base member is disposed under the patient, such that the support portion is disposed between the body of the patient and the operating table. Accordingly, in some embodiments, the base member of the medical device is coupled or removably coupled to the operating table.

At 420, the adjustable member is moved with respect to the base member. In some embodiments, the adjustable member is slid with respect to the base member.

At 430, a medical tool is inserted into a body of a patient. In some embodiments, the medical tool is coupled to the adjustment member. In some embodiments, a distal end portion of the medical tool is inserted into a body of the patient. For example, in some embodiments, the distal end portion of the medical device is inserted into a vagina of the patient.

In some embodiment, the method includes expanding the distal end portion of the medical tool from a first configuration to a larger, second configuration. In some embodiments, the expanding occurs after the insertion of the device into the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
   a base member including a first end portion and a second end portion; and
   an adjustment member being slideably and rotatably connected to the base member,
   wherein the base member configured to extend in a first direction and the adjustment member configured to extend in a second direction, the second direction being substantially orthogonal to the first direction,
   the base member includes a first surface portion and a second surface portion opposite the first surface portion, the first surface portion being disposed on a surface of an operating table and the second surface portion being adjacent to the adjustment member,
   the adjustment member having a body portion and a coupling portion, the coupling portion being removably coupled to the body portion, the coupling portion being configured to couple a medical tool to the adjustment member, at least a portion of the medical tool being configured to be inserted into a vagina of a patient.

2. The medical device of claim 1, wherein the coupling portion of the adjustment member is slidably coupled to the body portion of the adjustment member.

3. The medical device of claim 1, wherein the coupling portion of the adjustment member is configured to be slidably coupled to the medical tool.

4. The medical device of claim 1, wherein the coupling portion of the adjustment member includes a lock member, the lock member being configured to move with respect to the body portion of the adjustment member.

5. The medical device of claim 1, further comprising:
   a control device, the control device configured to remotely move the adjustment member with respect to the base member.

6. The medical device of claim 1, wherein an entire portion of the adjustment member is configured to move with respect to the base member.

7. The medical device of claim 1, wherein the adjustment member is directly coupled to the base member.

8. The medical device of claim 1, further comprising a retention member in the coupling portion to hold a position of the medical tool.

9. The medical device of claim 8, wherein the retention member is configured to move with respect to the adjustment member.

10. A medical device, comprising:
    a base member including a first end portion and a second end portion;
    an adjustment member being slideably and rotatably connected to the base member,
    wherein the base member is configured to extend in a first direction and the adjustment member is configured to extend in a second direction, the second direction being substantially orthogonal to the first direction,
    the base member includes a first surface portion and a second surface portion opposite the first surface portion, the first surface portion being disposed on a surface of an operating table and the second surface portion being adjacent to the adjustment member,
    the adjustment member having a body portion and a coupling portion, the coupling portion being removably coupled to the body portion; and
    a medical tool, the medical tool being movably coupled to the adjustment member, at least a portion of the medical tool being configured to be inserted into a vagina of a patient.

11. The medical device of claim 10, wherein the medical tool is removably coupled to the adjustment member.

12. The medical device of claim 10, wherein the coupling portion of the adjustment member is configured to move with respect to the body portion of the adjustment member.

13. The medical device of claim 10, wherein the coupling portion of the adjustment member is slidably coupled to the body portion of the adjustment member.

14. A method, comprising:
    placing a medical device near a patient, the medical device having a base member and an adjustable member, the base member including a first end portion and a second end portion, the base member being configured to extend in a first direction and the adjustment member being configured to extend in a second direction, the second direction being substantially orthogonal to the first direction;
    slideably and rotatably moving the adjustable member with respect to the base member such that the adjustment member is configured to move from a first positon between the first end portion and the second end portion to a second position between the first end portion and the second end portion; and
    inserting a medical tool coupled to the adjustable member into a vagina of the patient, the medical tool having a first configuration and a second configuration, the second configuration being different than the first configuration.

* * * * *